United States Patent [19]

Girzadas

[11] Patent Number: 4,867,139
[45] Date of Patent: Sep. 19, 1989

[54] HANDS-FREE SURGICAL INSTRUMENT FOR RETRACTING MUSCLES AND TISSUES

[76] Inventor: Daniel V. Girzadas, 20 Burris Ct., Palos Heights, Ill. 60453

[21] Appl. No.: 153,223

[22] Filed: Feb. 8, 1988

[51] Int. Cl.$^4$ .............................................. A61B 17/02
[52] U.S. Cl. ........................................ 128/20; 128/3; 128/303 R; 128/346
[58] Field of Search ............. 128/18, 20, 20 R, 303 R, 128/341, 346, 3

[56] References Cited

U.S. PATENT DOCUMENTS

| | | | |
|---|---|---|---|
| 3,747,592 | 7/1973 | Santos | 128/20 |
| 4,747,395 | 5/1988 | Brief | 128/20 |

FOREIGN PATENT DOCUMENTS 511203  3/1920  France .................... 128/20

Primary Examiner—Michael H. Thaler
Assistant Examiner—William W. Lewis
Attorney, Agent, or Firm—Kirkland & Ellis

[57] ABSTRACT

A surgical instrument is disclosed which can be clamped onto a bone, held in place without the need of a surgical assistant, and which retracts the muscles and tissues away from the bone also without the need of a surgical assistant. In the preferred embodiment of the present invention, the surgical instrument is designed for use on the femur of the hip during hip pinning surgery. In alternative embodiments of the present invention, the surgical instrument can be made into different sizes and shapes for utilization on any bone of the body so as to assist in the surgical exposure thereof.

7 Claims, 2 Drawing Sheets

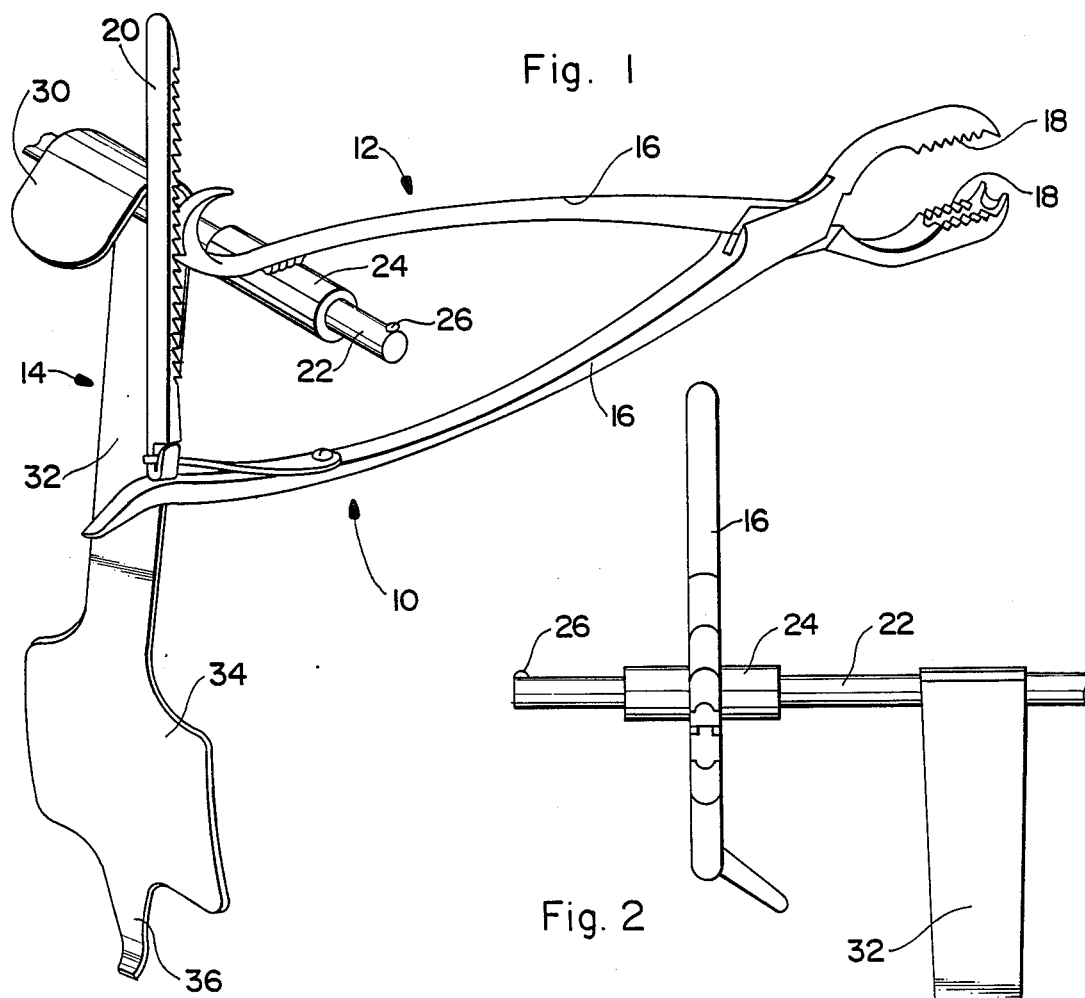
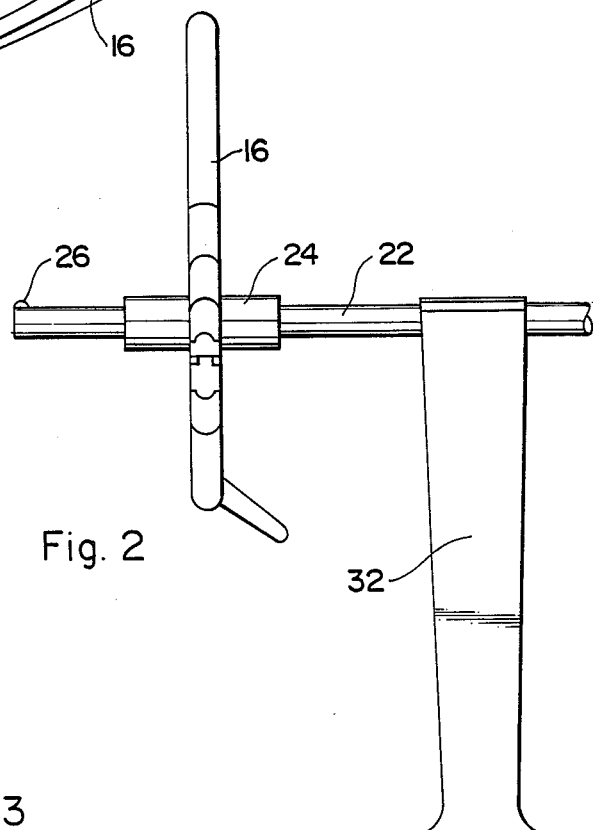
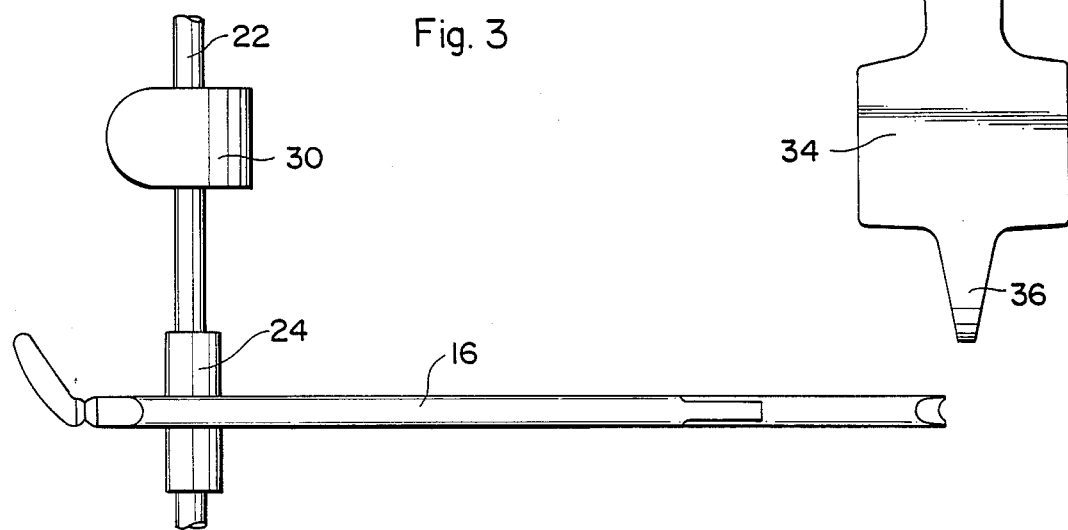
Fig. 1
Fig. 2
Fig. 3

4,867,139

HANDS-FREE SURGICAL INSTRUMENT FOR RETRACTING MUSCLES AND TISSUES

BACKGROUND OF THE INVENTION

1. Field of the Invention

This invention relates to surgical instruments and, more specifically, to an instrument used during surgical procedures to retract muscles and tissues from the bone being operated upon without the need of an assistant to hold the instrument in place.

2. Description of the Prior Art

During the course of a surgical operation, such as hip pinning surgery, it is necessary for a surgical assistant to retract the muscles and tissues away from the lateral side of the femur of the hip so that the surgeon can view the structures to be operated upon. Currently, such muscles and tissues are held away from the lateral side of the femur of the hip by a commercially available retractor such as a Bennett Retractor.

This prior art retractor for holding the muscles and tissues away from the bone being operated upon has several disadvantages. For example, in order to retract the muscles and tissues, a surgical assistant must physically hold the retractor in position. Occasionally, a surgical assistant is not available and a surgical scrub nurse must hold the retractor, thereby limiting her ability to perform other necessary tasks that a surgical scrub nurse must perform during the course of an operation. Another disadvantage of the prior art retractor is that it creates a radiation risk to its holder's hands stemming from x-rays that must be taken during the course of the operation while the instrument is held in position.

Thus, it is a principal object of the present invention to provide a surgical instrument to retract muscles and tissues away from the bone being operated upon without the need of a surgical assistant or other person to hold it in position.

It is another object of the present invention to reduce the radiation risk to surgical assistants from x-rays taken during the course of an operation.

It is another object of the present invention to achieve a cost saving advantage due to the elimination of the need for an assistant.

SUMMARY OF THE INVENTION

The above and other objects of the present invention are achieved by a hands-free surgical instrument which can be clamped onto a bone, such as the femur, held in place without the need of a surgical assistant or other person to hold it in position, and which retracts the muscles and tissues away from the bone also without the need of being manually held in position. In the preferred embodiment of the present invention, the hands-free surgical instrument comprises a scissor-like clamp having a pair of arms with a rod slidably attached to one of the arms; a ratchet attached to one of the arms which is capable of holding the scissor-like clamp in place around the bond to which it is clamped; and a broad blade type device which slips behind the bone being operated upon and retracts the muscles and tissues away from that bone. This blade type device hooks over the rod which is slidably attached to one arm of the scissor-like clamp. Once hooked over the rod, the blade, which also has a tip to anchor behind the bone, is held in position without the need of a surgical assistant or other person.

In alternative embodiments of the present invention, the hands-free surgical instrument can be made into different sizes and shapes for utilization on an bone of the body so as to assist in the surgical exposure thereof.

BRIEF DESCRIPTION OF THE DRAWINGS

The above and other objects of the present invention may be understood best by studying the following detailed description of the preferred embodiment, which description references the accompanying drawings, in which:

FIG. 1 is a perspective view of the hands-free surgical instrument of the present invention;

FIG. 2 is a front view of the hands-free surgical instrument of the present invention;

FIG. 3 is a top view of the hands-free surgical instrument of the present invention.

DETAILED DESCRIPTION OF THE PREFERRED EMBODIMENT

Figure 4:
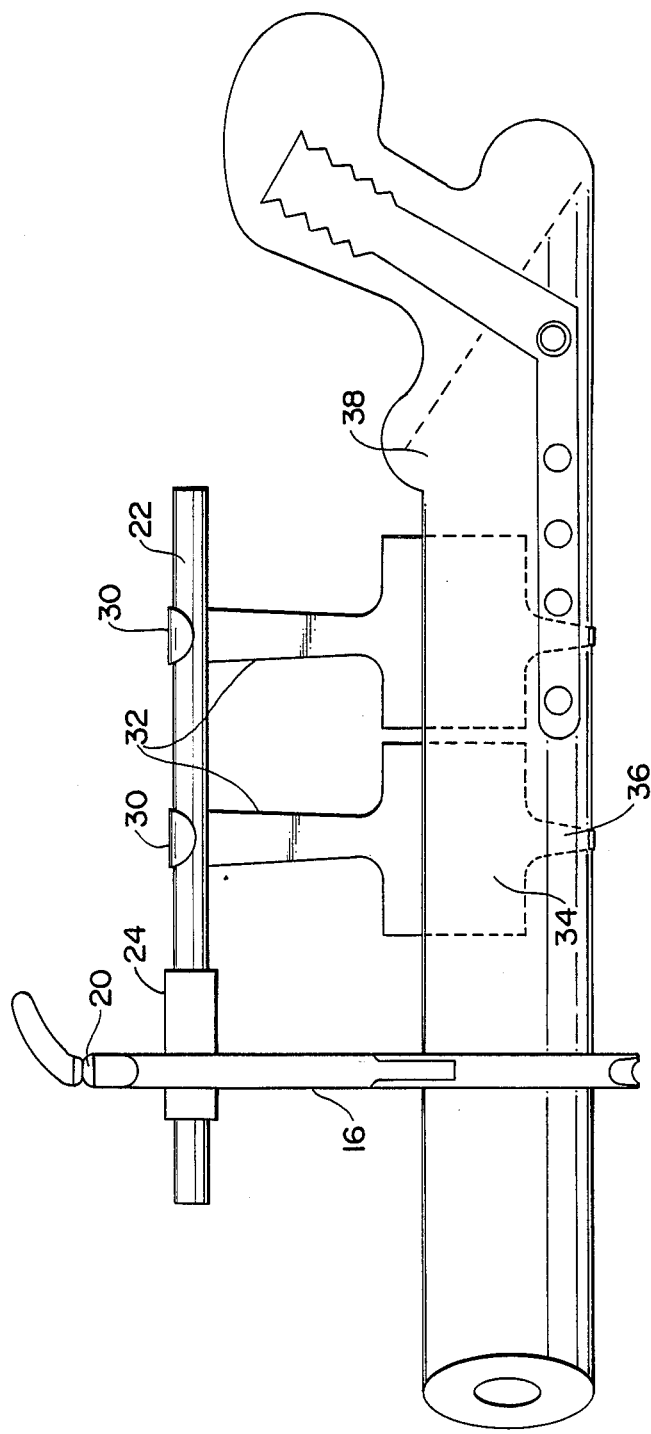
FIG. 4 is a perspective view of the hands-free surgical instrument of the present invention as used during a standard lateral incision for a hip pinning procedure.

With reference to FIGS. 1-3, hands-free surgical instrument 10 of the present invention is shown comprising pliers-like clamp 12, blade 14 and ratchet 20. Clamp 12 further comprises a pair of handles 16, one end of each having teeth 18. In the preferred embodiment, clamp 12 is a standard Lane type clamp, however, it should be understood that any suitable clamp with a ratchet could be used herein. Teeth 18 are adapted to be clamped onto a bone (not shown), such as a femur, so as to hold the clamp in position with respect to the bone during a surgical procedure. Ratchet 20, which is attached to one handle 16 of clamp 12, is used to maintain constant pressure of teeth 18 on the bone.

In the present invention, the otherwise standard clamp 12 is modified by the addition of a sleeve 24, through which rod 22 is slidably inserted. Sleeve 24 is rigidly attached to the underside of handle 16 preferably by welding. It should be understood, however, that other suitable means could be used to rigidly attach sleeve 24 to handle 16 without departing from the invention. The ends of rod 22 have screws 26 or other suitable members for preventing sleeve 24 of clamp 12 from sliding off the end of rod 22. Screws 26 can be removed so that rod 22 may be taken out of sleeve 24 for ease of storage. Handle 16 is pivotally mounted about shaft 22 by means of sleeve 24.

The present invention combines the clamp 12 with a blade 14, which has a hook 30 on one end of stem 32 for hanging blade 14 over shaft 22 so that blade 14 can pivot about shaft 22. A plate 34 for holding muscles and other tissues is located at the opposite end of stem 32. The end of plate 34 has a narrow tip 36 to anchor behind the bone. As seen in FIG. 4, plate 34 slips behind bone 38 (the bone being held by clamp 12) and retracts the muscles and other tissues (not shown) away from bone 38, allowing the surgeon and assistant to view the portion of the body being operated upon. In the preferred embodiment, the length of stem 32 is approximately the same as the length of handles 16 of clamp 12. Hook 30 rests upon shaft 22 which holds blade 14 in place thereby holding the muscles and tissues away from bone 38 without the need for a surgical assistant to physically hold blade 14.

The hands-free surgical instrument of the present invention can be positioned so that an x-ray unit (not shown), such as a C-arm x-ray unit, can be positioned without impedance of the surgical instrument and without exposing the surgical assistant to any unnecessary radiation risk while the x-rays are being taken.

It should be noted that the above description and drawings are illustrative only, as one of ordinary skill in the art would recognize, that various modifications could be made without departing from the spirit or scope of the present invention, which is to be limited only by the following claims.

What is claimed is:

1. A surgical instrument for retracting muscles and other tissues during surgical procedures without the need to hold it in place manually which comprises:
   a pair of pivotably mounted jaws adapted for being closed about a bone, each jaw having a protruding handle;
   a blade for retracting the muscles and tissues away from the bone, said blade having a pivotable mounting member on one end thereof;
   a rod adapted to cooperate with said pivotable mounting member such that said blade is pivotably supported by said rod;
   mounting means for pivotably mounting said rod onto one of the handles of said jaws; and
   clamp means for maintaining the handles of the jaws in a fixed position so as to apply uniform pressure of said jaws about the bone and for holding said rod and said blade in a fixed position with respect to the bone.

2. A surgical instrument as claimed in claim 1 wherein said pivotable mounting member further comprises:
   hook means for resting said blade on said rod such that said blade holds said muscles and tissues apart without the need of an assistant.

3. A surgical instrument as claimed in claim 1 wherein said blade further comprises:
   anchoring means for securing said blade behind the bone.

4. A surgical instrument as claimed in claim 1 wherein said clamp means further comprises:
   ratchet means pivotably attached to one of said handles and detachably mounted to the other of said handles.

5. A surgical instrument as claimed in claim 4 wherein said ratchet means further comprises:
   a bar having teeth on one side thereof, one end of said bar being pivotably attached to one of said handles; and
   a pawl member on one end of the other of said handles being adapted to receive said shaft therethrough.

6. A surgical instrument as claimed in claim 1 wherein said mounting means further comprises:
   a sleeve fixedly attached to one of the handles of said jaws, said sleeve being adapted to receive said shaft therethrough.

7. A surgical instrument as claimed in claim 1 wherein said blade is configured so as to hold the muscles and other tissues in a desired position with respect to the bone while said clamp means is clamped about the bone.

* * * * *

UNITED STATES PATENT AND TRADEMARK OFFICE
CERTIFICATE OF CORRECTION

PATENT NO. : 4,867,139
DATED : September 19, 1989
INVENTOR(S) : Daniel V. GIRZADAS It is certified that error appears in the above—identified patent and that said Letters Patent is hereby corrected as shown below:

In the Summary of the Invention:

Column 1, Line 60; "bond" should be -- bone -- and,

Column 2, Line 3; "an" should be -- any --.

Signed and Sealed this

Twenty-fifth Day of September, 1990

Attest:

HARRY F. MANBECK, JR.

*Attesting Officer*     *Commissioner of Patents and Trademarks*

UNITED STATES PATENT AND TRADEMARK OFFICE
CERTIFICATE OF CORRECTION

PATENT NO. : 4,867,139
DATED : September 19, 1989
INVENTOR(S) : DANIEL V. GIRZADAS It is certified that error appears in the above-identified patent and that said Letters Patent is hereby corrected as shown below:

On the title page

In the Inventor's Address:

"60453" should be --60463--.

Signed and Sealed this

Seventeenth Day of December, 1991

*Attest:*

HARRY F. MANBECK, JR.

*Attesting Officer*     *Commissioner of Patents and Trademarks*